United States Patent
Mukaidani et al.

(10) Patent No.: US 7,220,839 B2
(45) Date of Patent: May 22, 2007

(54) ANTIBODY RECOGNIZING PROLIFERATIVE HUMAN LIVER CELLS, PROLIFERATIVE HUMAN LIVER CELLS AND FUNCTIONAL HUMAN LIVER CELLS

(75) Inventors: Chise Mukaidani, Hiroshima (JP); Katsutoshi Yoshizato, Hiroshima (JP); Chihiro Yamasaki, Hiroshima (JP)

(73) Assignees: Japan Science and Technology Agency, Saitama (JP); Hiroshima Industrial Promotion Organization, Hiroshima (JP)

( * ) Notice: Subject to any disclaimer, the term of this patent is extended or adjusted under 35 U.S.C. 154(b) by 0 days.

(21) Appl. No.: 10/509,096

(22) PCT Filed: Mar. 25, 2003

(86) PCT No.: PCT/JP03/03624

§ 371 (c)(1),
(2), (4) Date: Feb. 9, 2005

(87) PCT Pub. No.: WO03/080670
PCT Pub. Date: Oct. 2, 2003

(65) Prior Publication Data
US 2005/0119463 A1 Jun. 2, 2005

(30) Foreign Application Priority Data
Mar. 25, 2002 (JP) .............................. 2002-084280

(51) Int. Cl.
*C07K 16/00* (2006.01)
*C12P 21/08* (2006.01)
*A61K 39/395* (2006.01)
*G01N 33/53* (2006.01)

(52) U.S. Cl. .............................. 530/388.1; 530/388.2; 435/7.2; 424/141.1; 424/152.1

(58) Field of Classification Search ............. 530/387.1; 424/130.1
See application file for complete search history.

(56) References Cited

FOREIGN PATENT DOCUMENTS

| EP | 682106 | 5/1996 |
| JP | 61-189299 | 8/1986 |
| WO | 00/43498 | 7/2000 |
| WO | 00/03001 | 1/2001 |

OTHER PUBLICATIONS

Flodby et al., "Increased Hepatic Cell Proliferation and Lung Abnormalities in Mice Deficient in CCAAT/Enhancer Binding Protein alpha," Oct. 1996, Journal of Biological Chemistry, 271(40): 24753-24760.*
Hilan et al. 1996. Journal of Hepatology 24:385-390.*
anti-Ki-monoclonal antibody information from Zymed (http://www.biocompare.com/itemdetails.asp?itemid=86403&catid=3194).*
Hillman et al (1996, Journal of Hepatology, 24:385-390).*
Zymed information sheet for anti-ki-67 monoclonal antibody.*
R. Jover et al., "Cytochrome P450 regulation by hepatocyte nuclear factor 4 in human hepatocytes: a study using adenovirus-mediated antisense targeting", Hepatology, vol. 33, No. 3, pp. 668-675, 2001.
D. Stroup et al., "HNF4 and COUP-TFII interact to modukate transcription of the cholesterol 7 alpha-hydroxylase gene (CYP7A1)", J. Lipid Res., vol. 41, No. 1, pp. 1-11, 2000.
S. Harish et al., "Transcriptional activation by hepatocyte nuclear factor-4 in a cell-free system derived from rat liver nucleic", Nucleic Acids Res., vol. 29, No. 5, pp. 1047-1053, 2001.

* cited by examiner

*Primary Examiner*—Shanon A. Foley
*Assistant Examiner*—Sean E Aeder
(74) *Attorney, Agent, or Firm*—Wenderoth, Lind & Ponack, L.L.P.

(57) ABSTRACT

The invention provides a monoclonal antibody which specifically recognizes proliferative human hepatocytes, a method for isolating proliferative human hepatocytes by using the antibody, and a method for inducing to differentiate the proliferative human hepatocytes to functional human hepatocytes. Further, the invention provides the proliferative human hepatocytes and functional human hepatocytes obtained by the methods, as well as a cell kit and a hybrid artificial liver comprising those hepatocytes.

3 Claims, 12 Drawing Sheets

Fig. 2
Human hepatocytes (12 years old) used as an antigen to prepare a monoclonal antibody
Primary culture
At 30 days
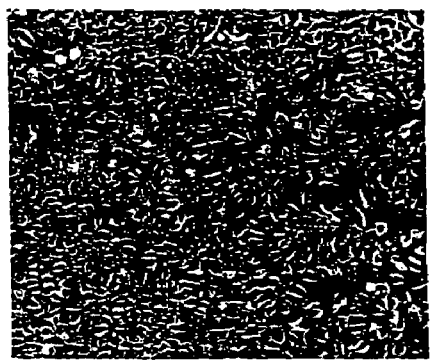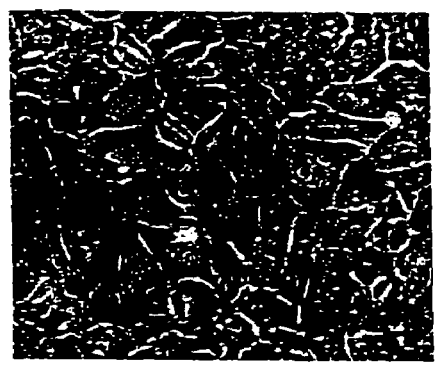
At 43 days
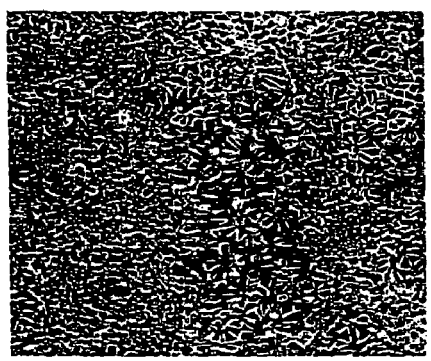
Subculture (3 passages)→immunizing mice
After 33 days
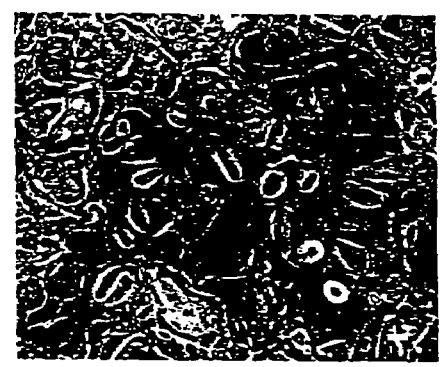
Bar, 100 μm

Fig. 3
Human tissue (62 years old)
Hybridoma culture supernatant (K8223)
K8223
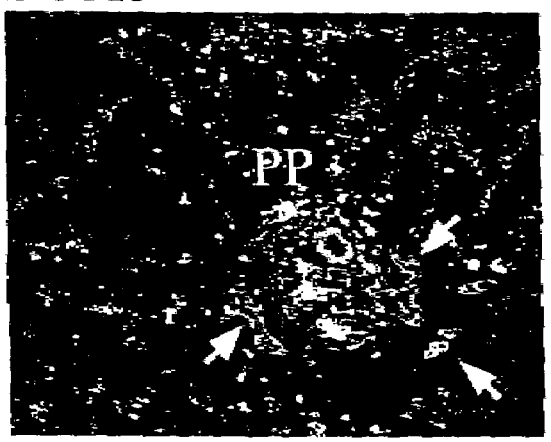
No primary antibody
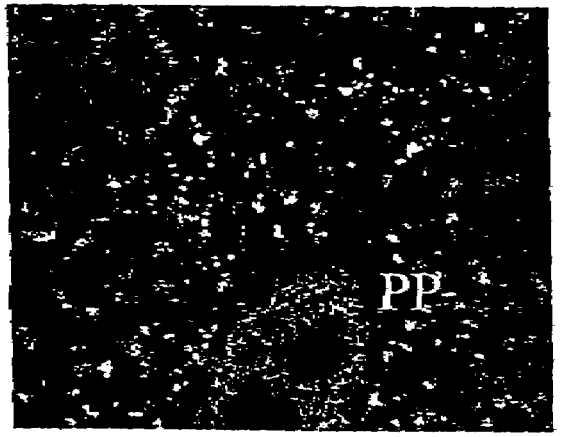
PP: Portal region
Bar, 50 μm Hybridoma culture supernatant: No.23
Isolated human hepatocytes (49 yeas old)

At day 1 in culture    At day 8 in culture

Before sorting

Bar, 100 μm

Fig. 5/1
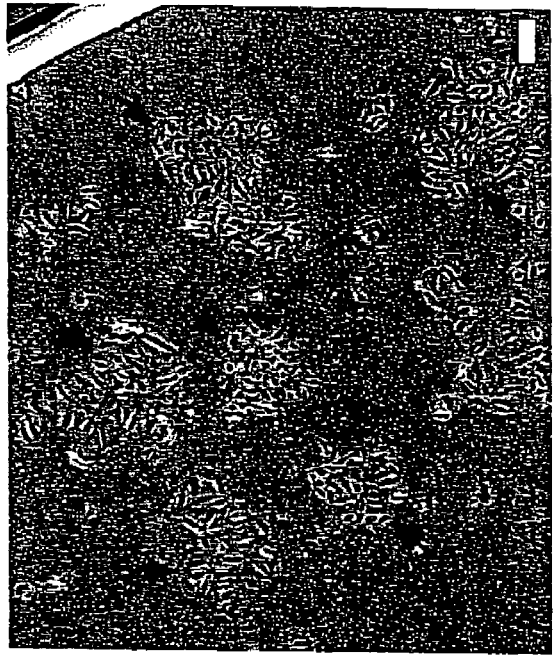
At day 8 in culture
Bar, 100 μm
Hybridoma culture supernatant: No.23
Isolated human hepatocytes (49 yeas old)
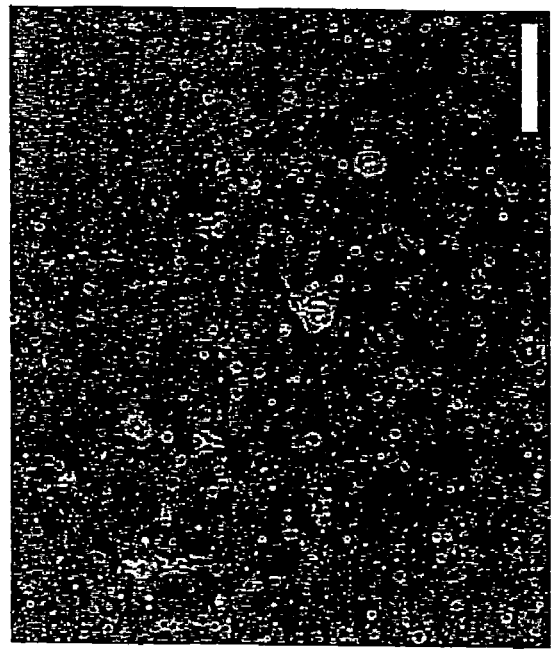
At day 1 in culture
R2 fraction

Fig. 5/2
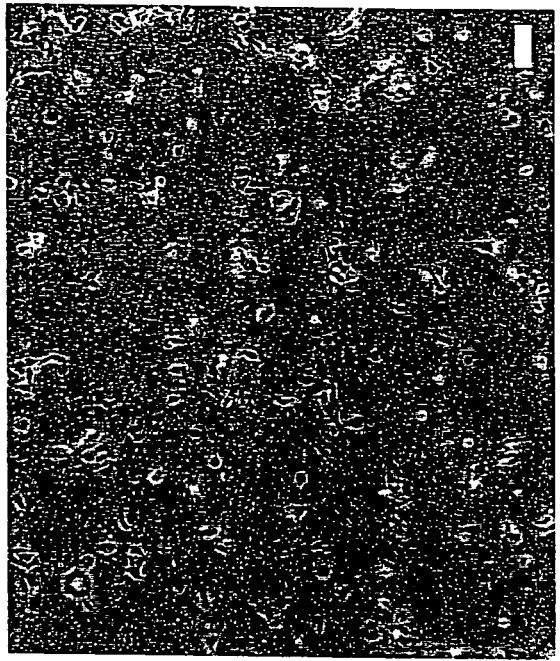
At day 8 in culture
Bar, 100 μm
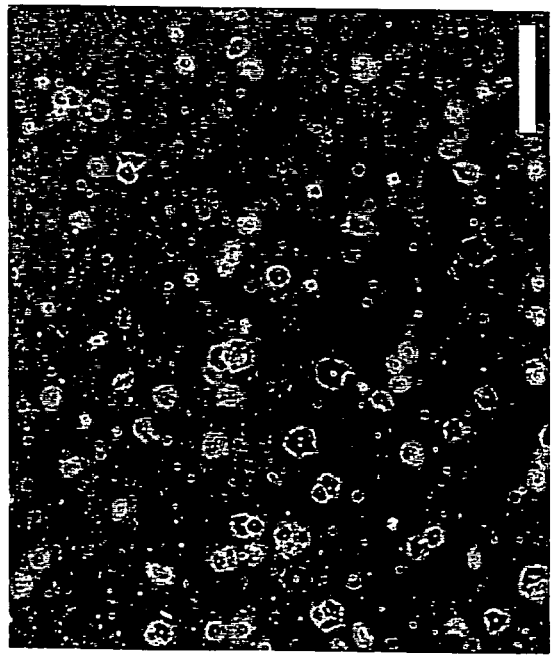
Hybridoma culture supernatant: No.23
Isolated human hepatocytes (49 yeas old)
At day 1 in culture
R3 fraction

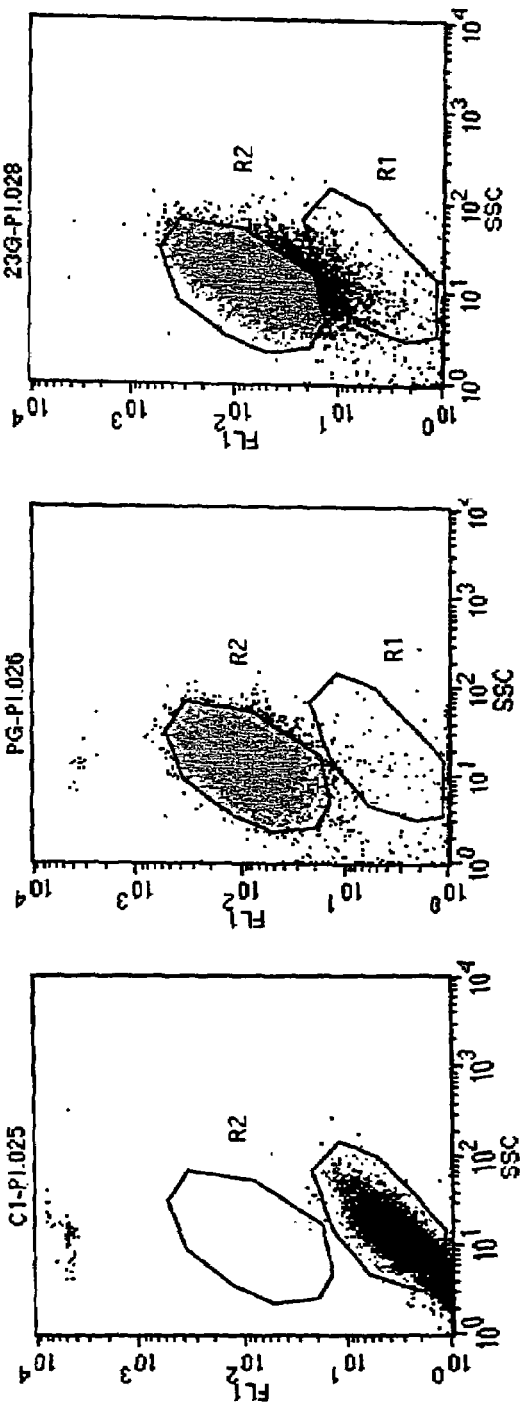

Fig. 8
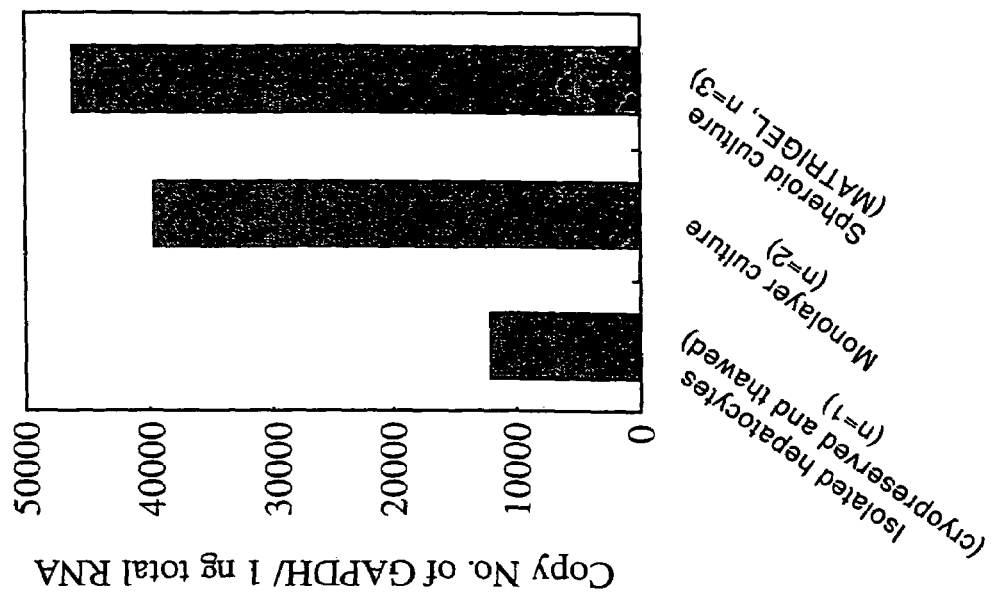
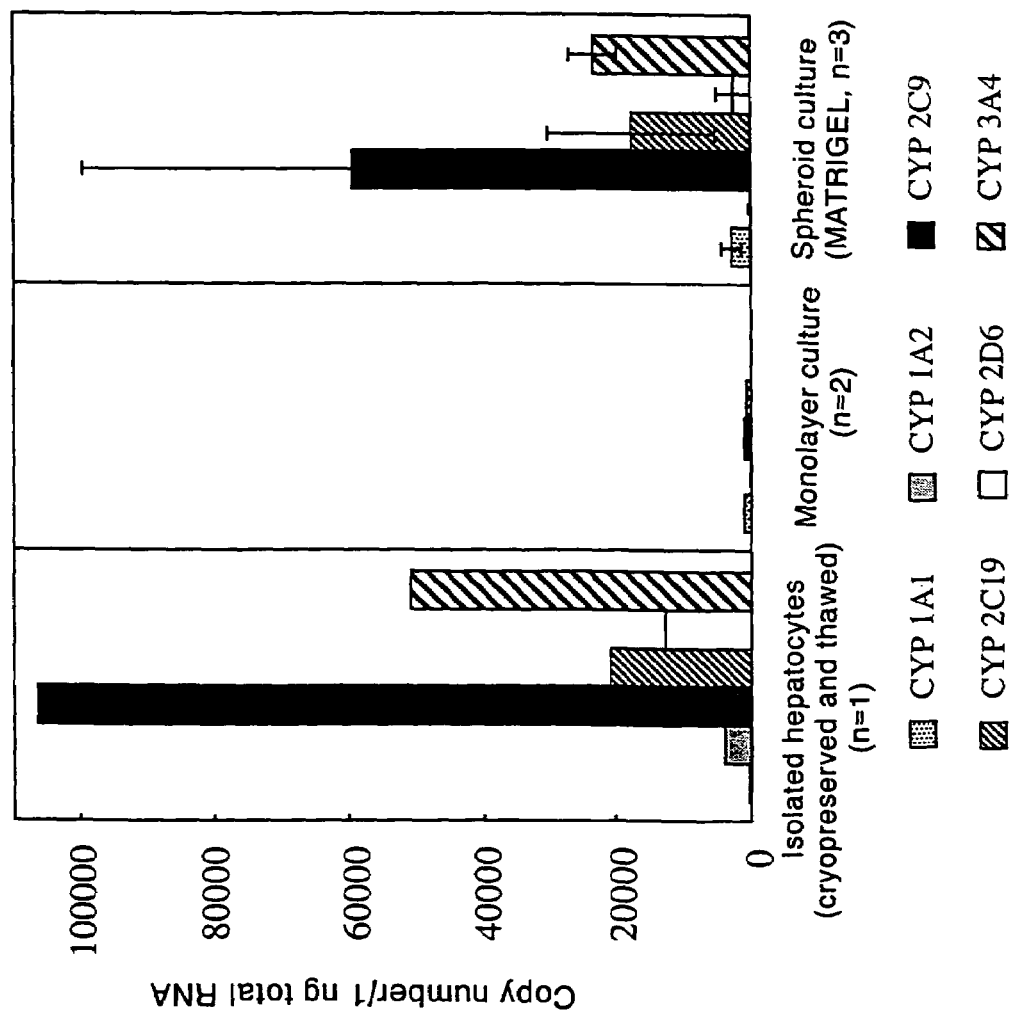

ANTIBODY RECOGNIZING PROLIFERATIVE HUMAN LIVER CELLS, PROLIFERATIVE HUMAN LIVER CELLS AND FUNCTIONAL HUMAN LIVER CELLS

TECHNICAL FIELD

The present invention relates to an antibody recognizing proliferative human hepatocytes, and human hepatocytes. More particularly, the present invention relates to a monoclonal antibody specifically recognizing human hepatocytes having clonal proliferative potency and useful for separating proliferative hepatocytes from a human hepatocyte population, proliferative human hepatocytes separated by using this antibody, a method of inducing the differentiation of the proliferative human hepatocytes to differentiated hepatocytes, functional human hepatocytes induced to differentiate by such a method, and a hepatocytes kit containing the functional hepatocytes and an extracorporeal artificial liver.

BACKGROUND ART

A liver has 500 or more types of various specific functions. Major functions of a liver include plasma protein synthesis and secretion, blood sugar control by gluconeogenesis and glycogen metabolism, lipogenesis, ureogenesis, bile synthesis and secretion and detoxication.

Most substances incorporated into a body are mainly metabolized in a liver. In the filed of pharmaceutical development, what type of metabolism pharmaceutical candidate substances will be received and what type of effect is given to a liver or other organs and tissues are essential data. Further, many chemical substances have been synthesized and discharged into environment up to now. To elucidate what kind of effect these substances have exerted individually or in combination to a human body is socially very important. Toxicological tests on liver function are essential for evaluation of the effects of such chemical substances to a human body.

Mice, rats, rabbits, dogs, monkeys, etc are used at present for safety tests and drug metabolism tests of chemical substances including pharmaceutical candidate substances. Especially in pharmaceutical development, toxicological tests and safety tests using animals are compulsive before entering phase I study for human, and long period and efforts as well as huge costs are required in these tests.

However, there is no guarantee that data obtained by these animal experiments can be applicable to human. In fact, many cases are known wherein substances not recognized toxicity in animal experiments exhibited toxicity in human or vice versa. Consequently, there might exist many cases wherein development of many pharmaceutical candidate substances were terminated after entering in phase I study on human, or also many substances were terminated development before entering clinical trials due to exhibiting strong toxicity in animal experiments but recognized actually no toxicity in human.

This may be caused by difference in metabolic function in a human liver and in metabolic function in livers of mice and rats. Recently, in vitro metabolic tests and toxicity tests using human hepatocytes have been performed. However, amount of livers from brain death patients which were not used for transplantation and amount of human hepatocytes obtained from hepatectomy in tumor excision are far fewer than demanded. Consequently, development of technology for human hepatocyte proliferation is essential for pharmaceutical development.

Necessity of high amount of human hepatocytes is very much alike in an extracorporeal artificial liver. The artificial liver is medical device acting liver function artificially. Development of a hybrid artificial liver combining with the artificial function based on physico-chemical principle such as adsorption, dialysis and filtration, along with biological actions using perfusion of an excised liver and liver tissue is strongly progressing. In development of the artificial liver, performance improvement of membrane and circuit to enhance physico-chemical function is essential, along with supplying high amount of hepatocytes applicable to human use.

However, subcultivation of primary cultured cells of a human liver isolated from adults has been considered impossible. Namely, the matured hepatocytes with adhesion dependency are largely damaged when cells are detached from culture substrate for subcultivation operation and are difficult to re-adhere to culture substrate. Contrary to that, the present inventors have invented a method for proliferative hepatocytes comprising isolating small hepatocytes, having clonal proliferative ability, from normal hepatocytes isolated from human liver, performing primary culture of the small hepatocytes, and subculturing further the cultured hepatocytes, and the invention was granted patents (JP-A-08-112092; JP No. 3266766; U.S. Pat. No. 6,004,810, JP-A-10-179148; JP No. 3211941, JP-A-07-274951; JP No. 3157984, and JP-A-09-313172; JP No. 3014322). Relating articles published are as follows: (Tateno, C. and Yoshizato, K.; "Growth and differentiation in culture of clonogenic hepatocytes that express both phenotypes of hepatocytes and biliary epithelial cells", Am. J. Phathol. 149: 1593–1605, 1996; Hino, H. Tateno, C. Sato, H. Yamasaki, C. Katayama, S. Kohashi, T. Aratani, A. Asahara, T. Dohi, K. and Yoshizato, K.; "A long-term culture of human hepatocytes which show a high growth potential and express their differentiated phenotypes", Biochem. and Biophys. Res. Commun. 256: 184–191, 1999; Tateno, C. Kajihara, K. T. Yamasaki, C. Sato, H. and Yoshizato, K. "Heterogeneity of growth potential of adult rat hepatocytes in vitro", Hepatology 31: 65–74, 2000; and Katayama, S. Tateno, C. Asahara, T. and Yoshizato, K.; "Size-dependent in vivo growth potential of adult rat hepatocytes", Am. J. Pathol. 158: 97–105, 2001).

The method of the above prior patented inventions provides novel means for obtaining high amount of human hepatocytes by proliferative hepatocytes in vitro, however, the human hepatocytes obtained by this method have a problem that various liver functions are impaired during long-term subculture. There is further a problem that the small hepatocytes can not differentiate to hepatocytes (functional hepatocytes) having function equivalent to normal hepatocytes, for example, albumin expression level and metabolic activity of cytochrome P450 for chemical substance and so on. By those reasons, they are still insufficient as hepatocytes for alternative human liver function or as a material for a hybrid artificial liver, although they are useful as a screening system of drugs for maintaining specific liver function or as a system for testing toxicity and pharmacological effect of drugs on specific functions which are conserved after long-term subculture.

Small hepatocytes having proliferation potency can be collected by using not only a method for centrifugal separation as described in the above prior patented invention (a method for separating cells in supernatant obtained by low speed centrifugation) but also a cell sorter such as an elutriator and FACS, however, cells obtained by such means are a mixture of not only proliferative hepatocytes but also other cells (such as non-hepatic parenchymal cells such as stellate cells contained in supernatant by low speed centrifugation). Consequently, means to obtain substantially proliferative human hepatocytes only has been required.

The present invention has been completed considering the above circumstances, and an aspect of the present invention is to provide a monoclonal antibody which specifically recognizes proliferative human hepatocytes.

Further, other aspect of the present invention is to provide a method for isolating proliferative human hepatocytes and the proliferative human hepatocytes obtained by such a method.

Further, other aspect of the present invention is to provide a method for inducing to differentiate the proliferative human hepatocytes to functional human hepatocytes, the functional human hepatocytes obtained by such a method and utilization of the functional human hepatocytes.

DISCLOSURE OF INVENTION

The present invention provides, as the first invention for solving the above problem, a monoclonal antibody specifically recognizing proliferative human hepatocytes. An example of a monoclonal antibody of the first invention is the monoclonal antibody produced by a hybridoma cell, Mouse-Mouse hybridoma K8223 (FERM BP-8334).

The second invention provides a hybridoma cell producing the monoclonal antibody of the first invention. An example of the hybridoma cell is Mouse-Mouse hybridoma K8223 (FERM BP-8334).

The third invention provides a method for isolating proliferative human hepatocytes, which comprises separating cells recognized by the monoclonal antibody of the first invention from a human hepatocyte population.

The fourth invention provides proliferative human hepatocytes isolated by the method of the third invention.

Further the fifth invention provides a method for inducing the differentiation of the proliferative human hepatocytes of the fourth invention, which comprises performing at least one of the following means:

(a) spheroid culture of the proliferative human hepatocytes; and (b) transfer of hepatic nuclear factor 4 (HNF4) gene into the proliferative human hepatocytes.

The sixth invention provides functional human hepatocytes induced to differentiate by the method of the fifth invention.

The seventh invention provides a cell kit comprising the functional human hepatocytes of the sixth invention.

The eighth invention provides a hybrid artificial liver filled with the functional human hepatocytes of the sixth invention.

In the present invention, a term "proliferative human hepatocytes" means human hepatocytes forming colonies as a population and proliferative so as to increase the colonies under in vitro culture condition. Further, "proliferation" may be designated as "clonal proliferation" because colony component cells are single species. Further, such cells can increase cell numbers by subculture.

In the present invention, a term "functional human hepatocytes" means cells having function level equivalent to that of human normal hepatocytes in human body (in vivo) or in the primary culture (in vitro) thereof, and more particularly, it means that at least level of "albumin expression" and "cytochrome P450 activity" thereof are substantially equal to those of human normal hepatocytes.

Other terms and concepts in the present invention will be defined in detail in the description of embodiments and examples of the present invention. Various techniques used for carrying out the present invention can easily be available based on known references by those skilled in the art except for those indicating specific sources thereof. For example, technologies of genetic engineering and molecular biology of the present invention are described in Sambrook and Maniatis, in "Molecular Cloning-A Laboratory Manual", Cold Spring Harbor Laboratory Press, New York, 1989; Ausubel, F. M. et al., "Current Protocols in Molecular Biology", John Wiley & Sons, New York, N.Y. 1995, etc.

BRIEF DESCRIPTION OF THE DRAWINGS

FIG. 2 is a phase-contrast microscopic images of cultured human hepatocytes used as an antigen for preparing a monoclonal antibody.

FIG. 3 is an image showing reactivity of culture supernatant of hybridoma K8223 on human liver tissues observed by immunofluorescence staining.

FIG. 6 is analysis result on reactivity of culture supernatant of hybridoma No. 23 on subcultured human hepatocyte surface, by FACS.

FIG. 8 is a graph exhibiting expression of human P450 gene or GAPDH gene on hepatocytes immediately after separation from a human liver, a monolayer cultured and spheroid cultured hepatocytes of subcultured hepatocytes, and spheroid cultured hepatocytes.

BEST MODE FOR CARRYING OUT THE INVENTION

Figure 1:
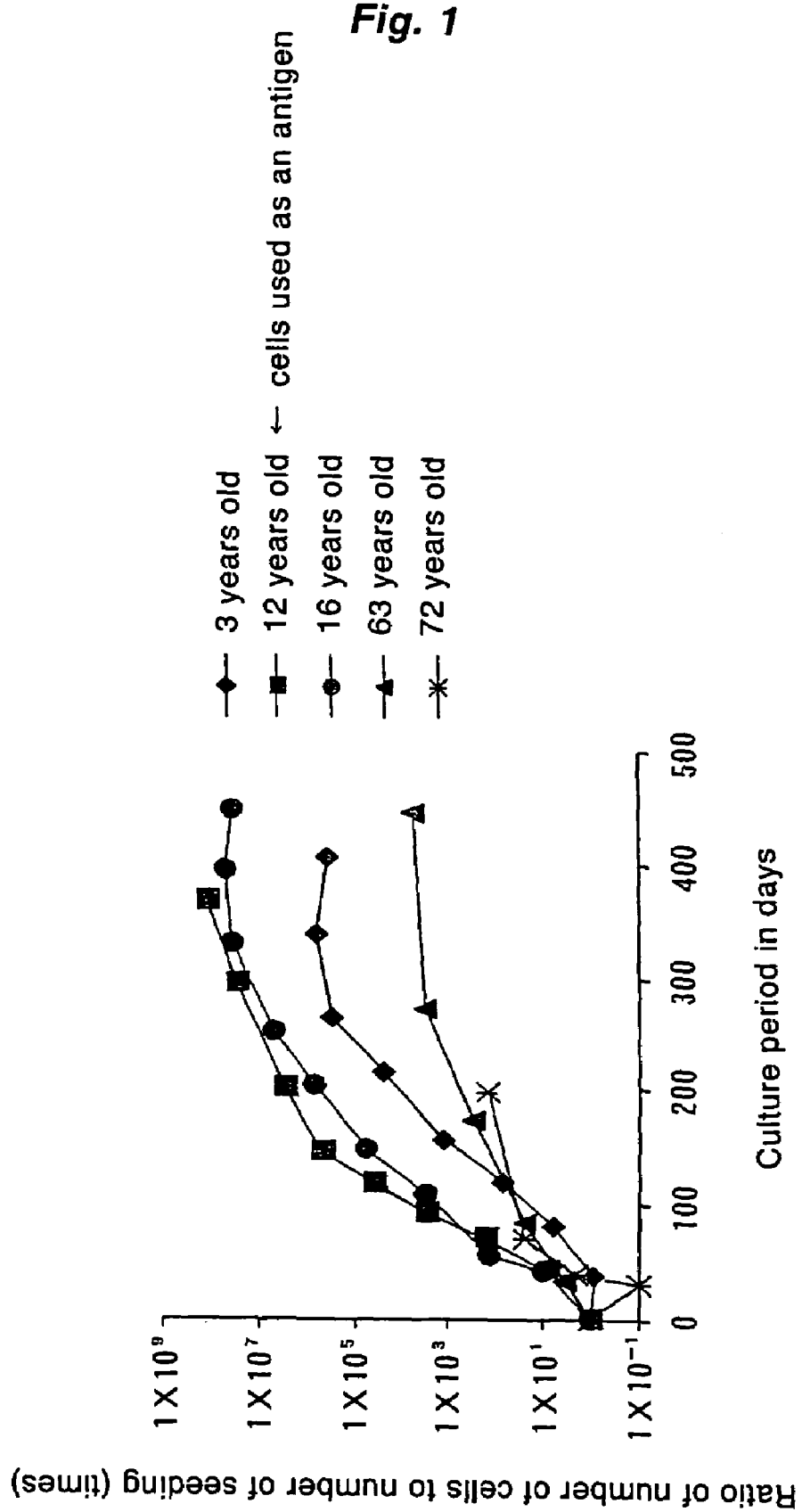
FIG. 1 illustrates a growth curve in culturing hepatocytes isolated from patients of various ages.

A monoclonal antibody of the first invention is characterized by specifically recognizing human hepatocytes proliferating while forming colonies. More particularly, the monoclonal antibody is characterized by specifically recognizing proliferative human hepatocytes while forming colonies and having potency of differentiating to functional human hepatocytes. In this case, a term "specifically recognizing" means to bind only to human hepatocytes defined hereinbefore and not to bind to other cells and/or human hepatocytes without having characteristics mentioned hereinbefore.

The monoclonal antibody of the first invention can be obtained from the hybridoma cells of the second invention by means of a known method. The hybridoma cells and the monoclonal antibody can be prepared according to a known method for preparation of a monoclonal antibody, described in "Monoclonal antibody", by Nagamune, K. and Terada, H.; Hirokawa Publ. Co., 1990, and "Monoclonal Antibody" James W. Goding, 3rd. Ed., Academic Press, 1996, for example, by the following procedures.

1. Preparation of Hybridoma Cells

Mammalians are immunized by using an immunogen containing subcultured human normal hepatocytes, and if necessary, animals are sufficiently sensitized by immunizing properly and additionally. Antibody producing cells (lymphocytes or spleen cells) are then isolated from the animals, and antibody producing cells and myeloma cell lines are fused to obtain hybrid cells. Cells which produce an objective monoclonal antibody are selected from these hybrid cell lines and cultured to obtain hybridoma cells. Each process is explained in detail below.

a) Preparation of an Immunogen

Human hepatocytes isolated from normal liver tissues using collagenase are subcultured to prepare an immunogen. The human hepatocytes isolated from human liver tissues of subjects not older than 15 years old, which are able to subculture for not less than 4 passages, preferably not less than 6 passages, are preferably used.

b) Immunization of Animals

Animals to be immunized can be mammals used for known hybridoma preparation and include typically, for example, mice, rats, goats, sheeps, equines and bovines. Mice or rats are preferable animals for immunization from the standpoint of easy availability of myeloma cells to be fused with separated antibody producing cells. There is no specific limitation on strains of mice and rats actually used, and strains of mice such as A, AKR, BALB/c, BDP, BA, CE, C3H, 57BL, C57BR, DBA, FL, HTH, HT1, LP, NZB, NZW, RF, RIII, SJL, SWR, WB and 129, and strains of rats such as Low, Lewis, Sprague, Daweley, ACI, BN and Fisher can be used. Considering compatibility with myeloma cells which will be explained hereinbelow, BALB/c strain for mouse and low strain for rat are particularly preferable for animals to be immunized. Ages of these mice and rats are preferably 5–12 weeks old.

Immunization of animals can be performed by administering subcultured human hepatocytes of the immunogen, about $10^4$–$10^8$ cells, intracutaneously or intraperitoneally into the animals. Administering schedule of the immunogen depends on types of animals to be immunized, individual differences, etc., however generally frequency of administering the immunogen is 1–6 times and an administering interval is 1–2 weeks in multiple administrations.

c) Cell Fusion

Spleen cells or lymphocytes containing antibody producing cells are aseptically collected from the animals to be immunized after 1–5 days from the final immunization date on the above administering schedule. Separation of the antibody producing cells from the spleen cells or the lymphocytes can be performed according to the known method.

The antibody producing cells and the myeloma cells are then fused. The myeloma cells used are not specifically limited and can be selected from known cell lines for use. However, considering convenience in selection of hybridoma from the fused cells, use of HGPRT (Hypoxanthine-guanine phosphoribosyltransferase) deficient strain, wherein selective procedure thereof has been established, is preferable. Namely, those are X63-Ag8(X63), NS1-Ag4/1(NS-1), P3X63-Ag8.U1(P3U1), X63-Ag8.653(X63.653), SP2/0-Ag14(SP2/0), MPC11-45.6TG1.7(45.6TG), FO, S149/5XXO, BU.1, etc. derived from mice; 210.RSY3.Ag.1.2.3 (Y3), etc. derived from rats; and U266AR(SKO-007), GM1500.GTG-A12(GM1500), UC729-6, LICR-LOW-HMy2(HMy2), 8226AR/NIP4-1(NP41), etc. derived from human.

Fusion of the antibody producing cells and the myeloma cells can be preferably performed under conditions without extremely reducing cell viability according to the known method. Such methods include, for example, a chemical method for admixing the antibody producing cells and the myeloma cells in a high concentration solution of polymer such as polyethylene glycol, and a physical method utilizing electric stimulation.

Selection of fused cells and non-fused cells are preferably performed, for example, by a known HAT (hypoxanthine-aminopterin-thymidine) selection method. This method is effective for obtaining fused cells by using the myeloma cells of HGPRT deficient strain which can not viable in the presence of aminopterin. Namely, fused cells with resistant to aminopterin can selectively be left and proliferated by culturing non-fused cells and fused cells in HAT medium.

d) Screening of Hybridoma

Screening of hybridoma cells producing an objective monoclonal antibody can be performed by known methods such as enzyme immunoassay (EIA), radio immunoassay (RIA) and fluorescent antibody technique.

The hybridoma cells producing a monoclonal antibody specifically bound to highly proliferative human hepatocytes can be obtained by such a screening method.

The screened hybridoma cells are cloned by known methods such as a methylcellulose method, a soft agarose method and a limiting dilution method and are used for antibody production.

The hybridoma cells obtained by methods explained hereinabove can be stored under freezing state in liquid nitrogen or a freezer at not higher than −80° C. The present application provides Mouse-Mouse hybridoma K8223 (FERM BP-8334), as a typical example of the hybridoma cell.

2. Obtaining a Monoclonal Antibody and Purification thereof

A monoclonal antibody specifically bound only to proliferative human hepatocytes can be obtained by culturing the hybridoma cells prepared in the above 1 step with a known method.

Cultivation can preferably be performed in medium having the same composition used in the above cloning method, or in a mouse intraperitoneally cultured by injecting the hybridoma cells and collecting the monoclonal antibody from ascites.

Thus obtained monoclonal antibody can be purified, for example, by ammonium sulfate fractionation, gel filtration, ion exchange chromatography and affinity chromatography methods.

The present application provides the above-described hybridoma cell, Mouse-Mouse hybridoma K8223 (FERM BP-8334) as a typical example of the hybridoma cells and a monoclonal antibody produced by the hybridoma cell, Mouse-Mouse hybridoma K8223 (FERM BP-8334), as a typical example of a monoclonal antibody.

The third invention relates to a separation method for proliferative human hepatocytes, and is characterized by isolating cells, which are recognized by the monoclonal antibody of the first invention, from a human hepatocyte population. The human hepatocyte population can be prepared, for example, as primary cultured cells, which are isolated from a human liver by a known method such as collagenase perfusion method and is cultured in vitro, or can be prepared as subcultured cells for 1–8 passages. Further, the human hepatocyte population can be "a cell population containing small human hepatocytes" disclosed in the patented inventions invented by the present inventors (JP-A-08-112092; JP No. 3266766; U.S. Pat. No. 6,004,810, JP-A-10-179148; JP No. 3211941, JP-A-07-274951; JP No. 3157984 and JP-A-09-313172; JP No. 3014322). That is, the small human hepatocytes in these patented inventions include non-parenchymal hepatocytes such as stellate cells or Swiss 3T3 cells which are co-cultured for culturing and subculturing small human hepatocytes. The proliferative human cells can be separated more efficiently from such cell populations by using the monoclonal antibody of the first invention.

Separation of the proliferative human hepatocytes can be performed by contacting the monoclonal antibody labeled with enzyme, radioisotope, magnetic beads or fluorescence with the above human hepatocyte population and separating cells indicating labeled signal. Since this method exhibits almost no cell loading caused by centrifugation, cell fractionation, etc., the proliferative human hepatocytes can be obtained without any damage. Enzyme used for labeling is not specifically limited, as long as it can satisfy conditions such as having large turnover number, exhibiting stability in binding to an antibody and specifically coloring substrate. Enzymes used for conventional EIA, such as peroxidase, β-galactosidase, alkaline phosphatase, glucose oxidase, acetylcholinesterase, glucose-6-phosphate dehydrogenase and malate dehydrogenase can be used. Enzyme inhibitors and coenzymes can also be used. Binding between an enzyme and an antibody can be achieved by a conventional method using a crosslinking agent such as a maleimide compound. With regard to substrate, known substance can be used depending on types of enzyme. For example, when peroxidase is used as an enzyme, 3,3',5,5'-tetramethylbenzidine can be used, and when alkaline phosphatase is used as an enzyme, such as p-nitrophenol can be used. With regard to a radioisotope, conventionally used radioisotope in RIA such as $^{125}$I and $^{3}$H can be used. With regard to a fluorescence pigment, those conventionally used for fluorescence antibody technique such as fluorescence isothiocyanate (FITC) and tetramethylrhodamine isothiocyanate (TRITC) can be used. When enzyme is used, detection of labeled signal can be performed by adding substrate, which develops color by decomposition due to enzyme action, followed by assaying enzyme activity by measuring the decomposed amount of the substrate by photometry, converting enzyme activity to an amount of bound antibody, and calculating the amount of an antibody by comparing with the standard value. When a radioisotope is used, radiation quantity emitted by the radioisotope is measured by using a scintillation counter, etc. When a fluorescence pigment is used, fluorescence yield is measured by apparatus combined with a fluorescence microscope.

According to the method described hereinabove, "the proliferative human hepatocytes" of the fourth invention can be obtained. The proliferative human hepatocytes grow actively while forming colonies under culture condition, and have differentiation potency to functional human hepatocytes. Such functional human hepatocytes can be induced to differentiate from the proliferative human hepatocytes by the method of the fifth invention. The functional human hepatocytes can also be obtained by the method for obtaining the human hepatocytes used as the immunogen in the preparation of the monoclonal antibody in Example 1, however, there is possibility to contain non-proliferative cells in the method of Example 1. The method using a monoclonal antibody in the present invention is an excellent method on the point that substantially the proliferative human hepatocytes only can be isolated.

The method according to the fifth invention is characterized by performing the following means (a) or (b), or (a) and (b).

(a) Spheroid Culture of Proliferative Human Hepatocytes

"Spheroid" means a cell population forming tissue structure by aggregation of several hundreds of cells. Typically, cells are collected to form a three-dimensional cell population by a method shown below and are cultured in an animal cell culture medium. Known methods for obtaining spheroid include culturing using Matrigel (MATRIGEL™ Matrix, Becton, Dickinson and Co.), a positive charged incubator (Primaria, Becton, Dickinson and Co.) and a U-shaped incubator (Spheroid MS-0096S, Sumiron) and rotary culture using a roller bottle. Culture is performed for about 6–15 days.

(b) Transfer of Hepatocyte Nuclear Factor 4 (HNF4) Gene Into Proliferative Human Hepatocytes Hepatocyte nuclear factor 4 (HNF4) is a protein relating to transcription of gene expressing specific function in hepatocytes (e.g. Bell, G. I. et al., Proc. Natl. Acad. Sci. USA 88(4), 1484–1488, 1991) and cDNA sequence of human HNF4α is known (e.g. GeneBank/NM_000457). cDNA sequences of HNF4b (GenBank/X87871) and HNF4c (GenBank/X87872) is also known. Mouse HNF4 cDNA (GenBank/NM_008261) and rat HNF4 cDNA (GenBank/X57133) are also known. Consequently, these known HNF4 cDNAs are recombined with a eukaryotic cell expression vector and the resultant expression vector is introduced into proliferative human hepatocytes by known method such as an electroporation method, a calcium phosphate transfection method, a liposome method and a DEAE dextran method, to introduce HNF4 gene. HNF4 gene can also be introduced by a method according to a gene therapy method (an ex vivo method) by using hollow nano-particles having a biorecognizing molecule, retro virus, lentivirus, adenovirus and adeno-associated virus. HNF4 gene cDNA can be obtained by screening human and other cDNA libraries using a probe DNA prepared based on known sequence thereof. Thus obtained cDNA can be used by amplifying with a conventionally used gene amplification method such as PCR (Polymerase Chain Reaction) method, NASBN (Nucleic acid sequence based amplification) method, TMA (Transcription-mediated amplification) method and SDA (Strand Displacement Amplification) method. Sufficient amount of objective cDNA can also be obtained by RT-PCR (Reverse Transcriptase-PCR) method with a template of mRNA isolated from mammalian cells using a primer set based on known sequence.

According to the above-described differentiation inducing method, as will be described in Examples hereinafter, the functional hepatocytes of the sixth invention having function level equivalent to that of human normal hepatocytes in vivo or in primary culture can be obtained, typically expressing sufficient amount of albumin and having sufficient cytochrome P450 activity. The functional human hepatocytes obtained by the above differentiation induction can be replaced, for example, by subcultured cells obtained by a similar method for preparing the immunogenic human hepatocytes in Example 1 (hepatocytes which can be subcultured while forming colonies). In such subcultured cells, non-proliferative cells may be contained.

The human hepatocytes kit (the seventh invention), which can be used for drug metabolizing tests and safety tests, and the hybrid artificial liver (the eighth invention) are provided by using the functional human hepatocytes of the sixth invention obtained by the above methods.

Various hepatocytes kits are known depending on types of cells and applications. Those skilled in the art can easily prepare the cell kit of the seventh invention by employing a constitution of the human hepatocytes of the sixth invention and a known cell kit. Further, a constitution of a module type or a hybrid type artificial organ is known, and those skilled in the art can easily prepare the artificial liver of the eighth invention.

EXAMPLES

The present invention in this application is explained by describing Examples in detail and concretely, however, the present invention is by no means limited thereto.

Example 1

Preparation of a Monoclonal Antibody Recognizing Human Proliferative Hepatocytes 1. Culture of Human Hepatocytes A cell suspension was obtained from human liver tissue by a collagenase perfusion method. The cell suspension was centrifuged in low speed (50 g, 2 min.). The precipitated fraction was co-cultured with mitomycin C treated Swiss 3T3 cells using Dulbecco's modified Eagle's medium (DMEM) added with fetal calf serum, human serum, EGF, nicotinamide and long-acting vitamin C derivative. Swiss 3T3 cells were added every ten days. Human hepatocyte colonies were observed after about 7 days of culture. Confluent growth hepatocytes were subcultured by using EDTA/Trypsin. Hepatocytes of children could be subcultured for 6–9 passages, however, hepatocytes of patients, not younger than 60 years old, could only be subcultured for 3–4 passages (FIG. 1). Hepatocytes of the child (12 years old) exhibiting the highest proliferation ability were used as an antigen (FIG. 2).

2. Immunization of Animals

The hepatocytes of the child (12 years old) subcultured for 3–5 passages by the above-described method were proliferated on culture dishes. After confluent growth cells (about $1 \times 10^7$ cells) were washed with PBS (a phosphate buffer salt solution), PBS was removed and the cells were recovered by scraping with a cell scraper to suspend in about 1 ml PBS. The suspension was administered intraperitoneally in Balb/c mice, 6 weeks old. Immunization was further performed by a similar method after 20 days or 30 days.

3. Cell Fusion

After twice immunization, increased antibody titer was observed. After 72 hours of the third immunization (boost), a spleen was extracted from an immunized animal to collect spleen cells. These spleen cells and mouse myeloma cells (Name of cell: NS-1) were fused, plating into 372 wells of a 96-well plate and cultured.

4. Screening of Hybridoma

Primary Screening (ELISA, Tissue Staining)

Reactivity of culture supernatant of the fused cells thus obtained to an antigen was assayed by ELISA. Assay was performed by the following method. The culture supernatant was treated with the subcultured hepatocytes, which were obtained by seeding the subcultured hepatocytes used, as an antigen, on the 96-well plate, followed by washing with PBS after cultivation, drying and storing at −80° C. An enzyme-labeled anti-mouse IgG antibody or an anti-mouse IgM antibody was then reacted therewith, followed by developing color by adding substrate to measure optical absorption. As the results, mean absorbance of 372 samples of the fused cell was 0.149 (SD: 0.099), and samples with absorbance of not lower than 0.20 (81 samples, about 20%) were defined as positive samples. Since color development was confirmed in naked eye observation in samples with absorbance of not lower than 0.15, samples with the absorbance of from 0.15 to 0.20 (46 samples) was treated with tissue staining to confirm reactivity. Among them, 13 samples showing interesting staining pattern were judged as positive samples. Selected 94 positive samples were further cultured in large scale, and culture supernatant was collected and cells were cryopreserved.

5. Secondary Screening (ELISA, Tissue Staining)

From 94 samples selected by the primary screening, 88 positive samples were selected by measuring reactivity against an antigen in culture supernatant after the large scale cultivation, by ELISA similarly as in the primary screening. Reactivity in tissue of these samples was studied by tissue staining. Samples containing hybridoma, which specifically reacts with cell membrane of hepatocytes and hepatocytes in portal region, or supernatant of the clone obtained by cloning therefrom, were studied on reactivity against freshly isolated human hepatocytes.

Figure 4:
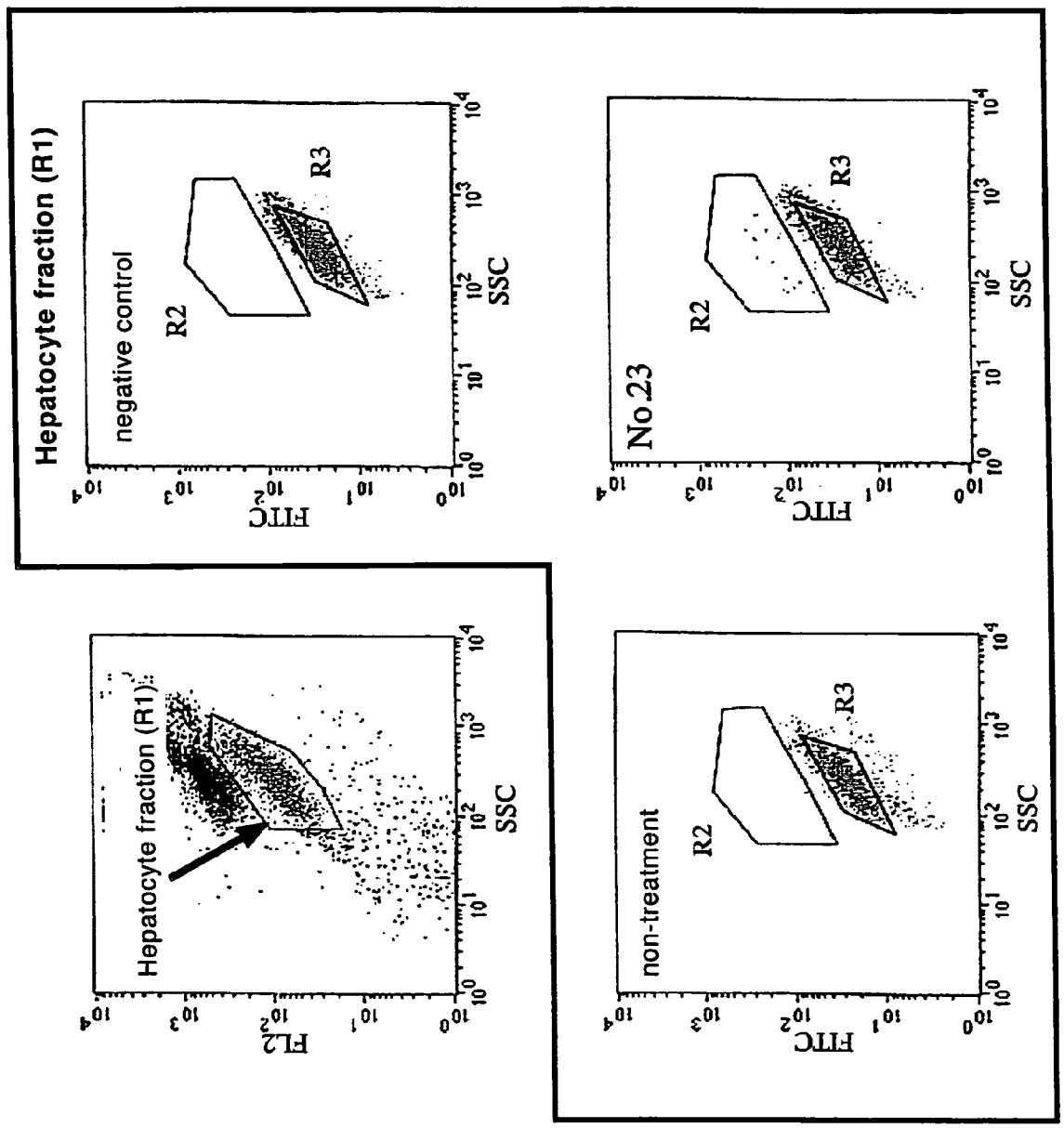
FIG. 4 is analysis result on reactivity of culture supernatant of hybridoma No. 23 on isolated human hepatocyte by FACS.
Figure 5:
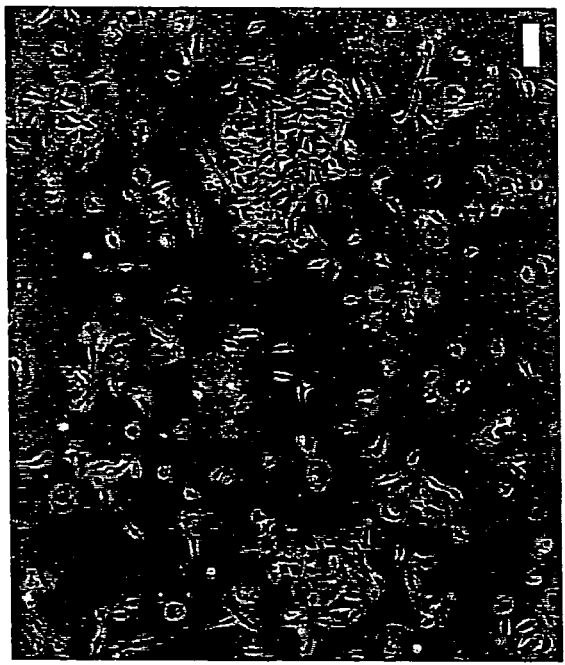
FIG. 5 is a phase-contrast microscopic images of cell populations which reacted, No. 23 (R2), and non-reacted (R3) with culture supernatant of hybridoma are sorted and cultured.

Supernatant No. 23 of cultured hybridoma, in which the hepatocyte membrane of the portal region was stained in a histological test, was analyzed on reactivity at cell surface of freshly isolated hepatocyte, by using FACS (fluorescence activated cell sorting). Hepatocytes of adult males, 46 years old and 49 years old, obtained by a collagenase perfusion method under low speed centrifugation, were treated with culture supernatant of this sample at 4° C. for 30 minutes, and an FITC labeled anti-mouse IgG antibody was then treated at 4° C. for 30 minutes to make detection by FACS possible. As the result, a part of cells (1–2%) in a hepatocyte population reacted with the sample (FIG. 4). The reacted cell population, designated as R2 fraction, and the non-reacted cell population, designated as R3 fraction, were sorted and cultured. Hepatocytes before fractionation were also cultured. As the result, colony formation was observed on culture of about 7 days in the hepatocytes before fractionation as described hereinbefore. On the other hand, colony-forming cells were not observed in the R3 fraction, but large numbers of colony were observed in the R2 fraction reacted with No. 23 (FIG. 5). Reactivity with the subcultured human hepatocytes was examined by FACS, and about 80% of the cells were found to be positive (FIG. 6). Namely, it was considered that among the subcultured human hepatocytes, the differentiated cells during culturing process were not recognized and only the proliferative hepatocytes were recognized. From these results, No. 23 was suggested to contain hybridoma which specifically recognized colony-forming cells. Clones obtained by cloning from No. 23 sample were analyzed by using FACS on reactivity at cell surface of freshly isolated hepatocytes. As the result, three clones showing similar reactivity were obtained. Among these clones, a clone (Mouse-Mouse hybridoma K8233) was deposited in The International Patent Organism Depositary, National Institute of Advanced Industrial Science and Technology (Deposition No. FERM P-18752) on Mar. 6, 2002, and was subjected to international deposition on Mar. 20, 2002 (Deposition No. FERM BP-8334).

6. Preparation of a Monoclonal Antibody

The above hybridoma cell (K8223 strain) was cultured, followed by intraperitoneal injection in mice and collection of a monoclonal antibody from ascites to obtain a monoclonal antibody which specifically binds to proliferative human hepatocytes.

Example 2

Isolation of Proliferative Human Hepatocytes

Using the monoclonal antibody obtained in Example 1, proliferative human hepatocytes were separated from the human hepatocyte population which was isolated from human liver tissue by a collagenase perfusion method. Concretely, said cells obtained from the human liver tissue by collagenase perfusion following low speed centrifugation were treated with the monoclonal antibody obtained in Example 1 at 4° C. for 30 minutes and an FITC labeled anti-mouse IgG antibody was treated at 4° C. for 30 minutes to detect reaction by FACS. The cell population reacted with this antibody, designated as R2 fraction, and the non-reacted cell population, designated as R3 fraction, were sorted and cultured similarly as in Example 1. The hepatocytes before sorting were also cultured. As the result, colony formation was observed on culture of about 7 days in the hepatocytes before fractionation. On the other hand, colony-forming cells were not observed in the R3 fraction, but large numbers of colony were observed in the R2 fraction reacted with this monoclonal antibody. From the above results, it was confirmed that proliferative hepatocytes could efficiently be isolated from a isolated hepatocyte population, using the method of the present invention.

Example 3

Differentiation Induction of Proliferative Human Hepatocytes by Spheroid Formation 1. Spheroid Formation of Hepatocytes The proliferative human hepatocytes obtained in Example 2 were seeded, $1 \times 10^5$ cells/cm$^2$, on matrigel (MATRIGEL™ Matrix, Becton, Dickinson and Co.) and cultured in DMEM medium added with fetal calf serum, EGF and long-acting vitamin C. The hepatocytes formed spheroid on the matrigel at 1 day of culture (FIG. 7, upper column).

2. Analysis of Human P450 Gene Expression

Figure 7:
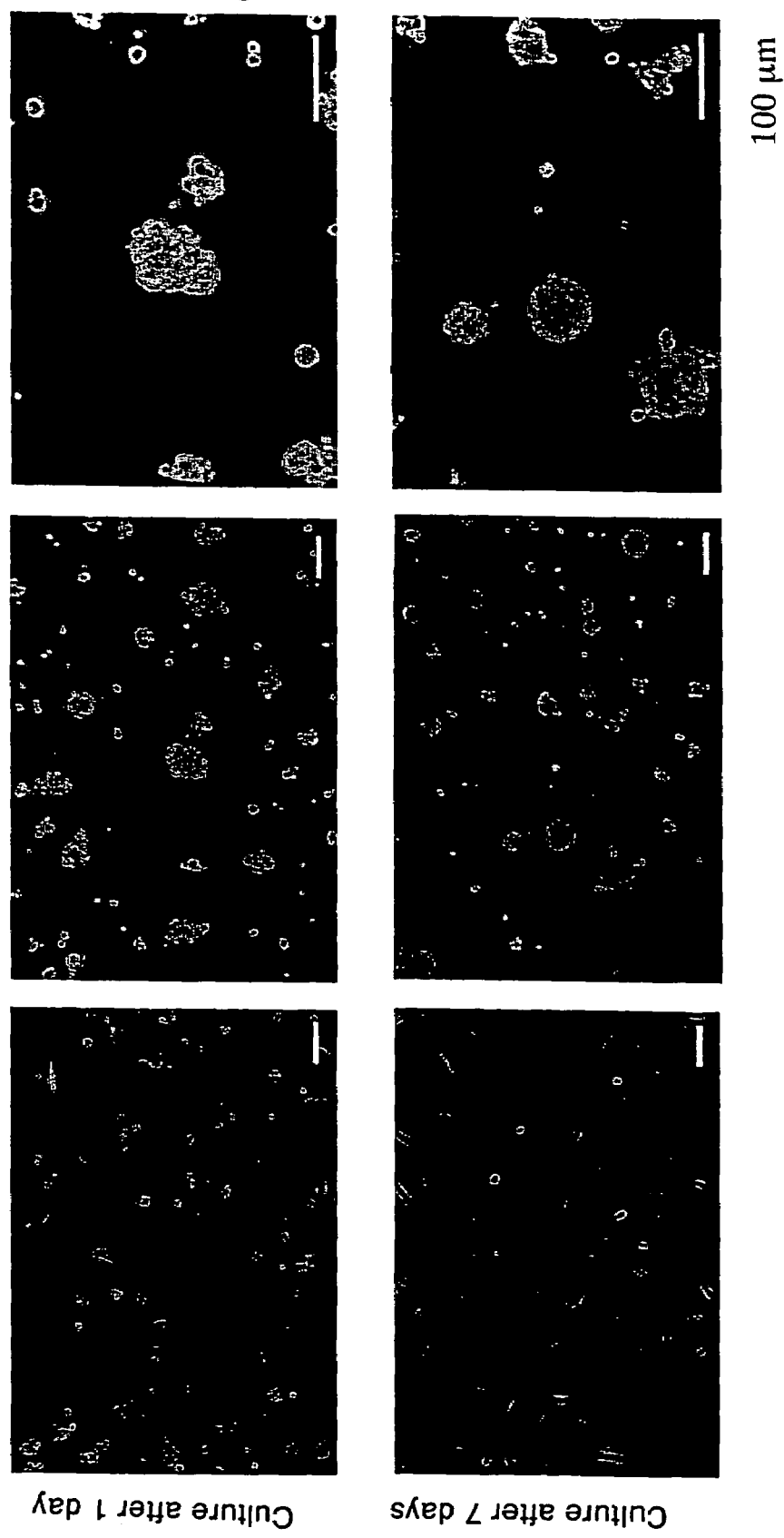
FIG. 7 is a phase-contrast microscopic images of monolayer culture and spheroid culture of hepatocytes after 1 day (upper column) and 7 days (lower column).

After seeding the cultured human hepatocytes on matrigel, the spheroid was recovered after 7 days (FIG. 7, lower column). Total RNA was extracted from the spheroidal hepatocytes, and cDNA was synthesized by reverse transcription reaction. Primers corresponding to each gene cDNA of six types of human P450 molecular species (CYP1A1, 1A2, 1C9, 2C19, 2D6 and 3A4) were synthesized, and expression amount of each mRNA was measured quantitatively by using PRISM 7700 Sequence Detector (ABI PRISM™, Applied Biosystems Co.). P450 gene expression was also quantitatively measured in the hepatocytes freshly isolated from a human liver and monolayer cultured proliferative human hepatocytes.

As the result, it was confirmed that spheroid cultured hepatocytes exhibited higher gene expression of each human P450 than monolayer cultured hepatocytes. Some human P450 genes exhibited P450 gene expression level equivalent to that of human normal hepatocytes freshly isolated (FIG. 8).

3. Analysis of Albumin Secretion

Each supernatant of the spheroid cultured hepatocytes and the monolayer cultured hepatocytes was collected on every 3 days and human albumin concentration in the culture medium was assayed by using Quantitative ELISA immunoassay (Bethyl Laboratories Inc.).

Figure 9:
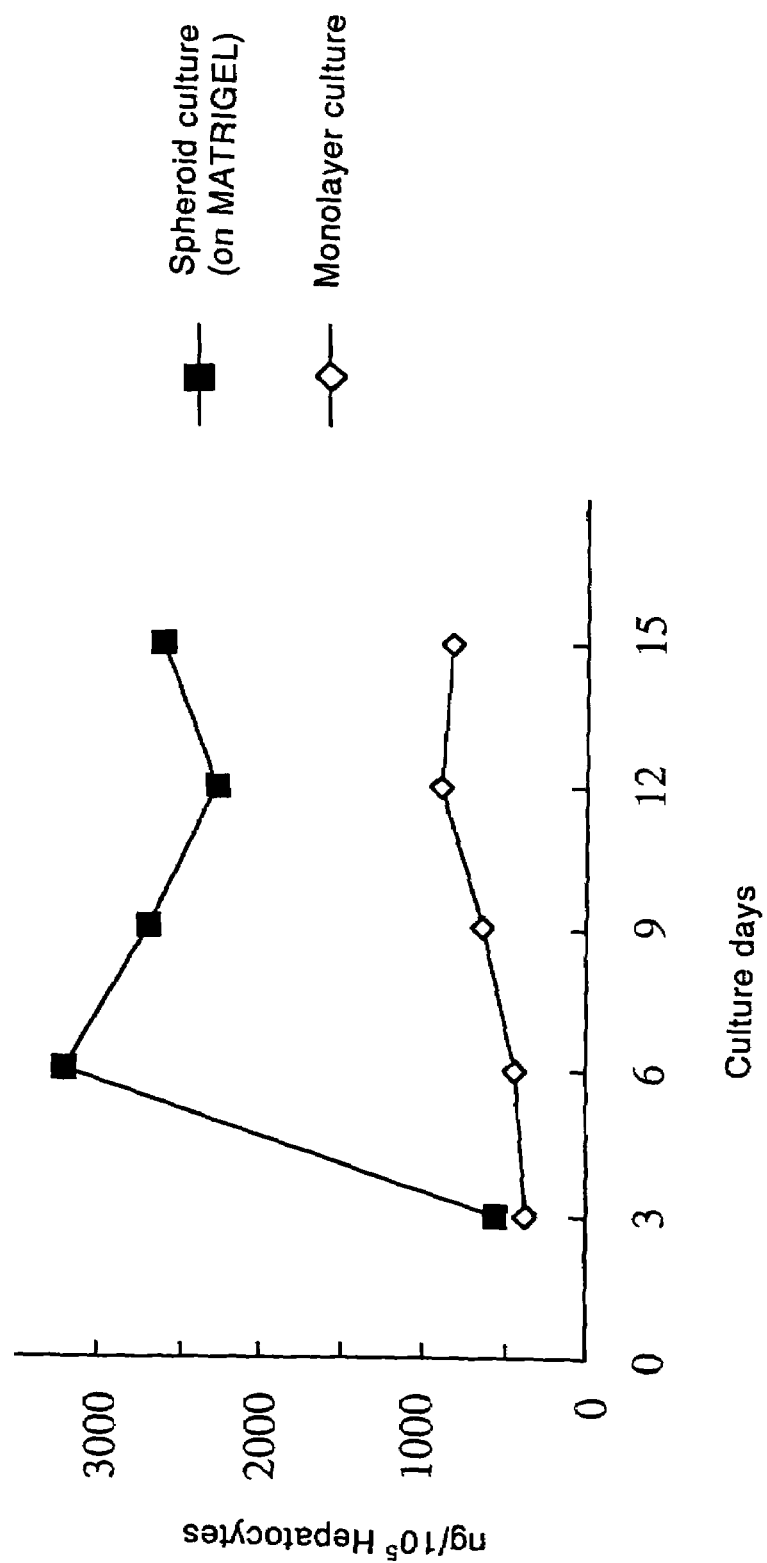
FIG. 9 is a graph showing time-dependent changes in albumin secretion from hepatocytes obtained by monolayer culture and spheroid culture.

As the result, the hepatocytes by spheroidal culture exhibited higher albumin secretion at culture period not shorter than 6 days as compared hepatocytes by monolayer culture (FIG. 9).

4. Analysis of P450 Enzyme Activity

On 22 days of the spheroid culture, lidocaine hydrochloride (500 μ/ml) was added to the culture medium and incubated for 24 hours. The medium was collected and amount of MEGX, a metabolite of lidocaine, in the medium was assayed by HPLC. Similar assay was performed on monolayer cultured hepatocytes.

As the result, MEGX was not detected in the medium of the monolayer cultured hepatocytes, but MEGX was detected in the medium of the spheroid cultured hepatocytes (8.3 μg/ml/24 hours, 1.7 μg/$10^5$ cells/24 hours). From this result, it was confirmed that the spheroid cultured hepatocytes have P450 enzyme activity (chemical substance metabolizing enzyme activity).

Example 4

Differentiation Induction of Proliferative Human Hepatocytes by HNF4 Gene Transfer 1. Gene Transfer The proliferative human hepatocytes obtained in Example 2 was infected with Human HNF4 α cDNA (GenBank/X87870) through an adenovirus vector (Qbiogene, Inc.) with a ratio of multiplicity of infection (MOI) 0, 1, 5, 10, 20, 50 and 100 on 1 day of the culture.

2. Analysis of Human P450 Gene Expression

Cells on 7 days after the adenovirus vector infection were collected, and expression of each human P450 gene was assayed quantitatively similarly as in Example 3-2.

Figure 10:
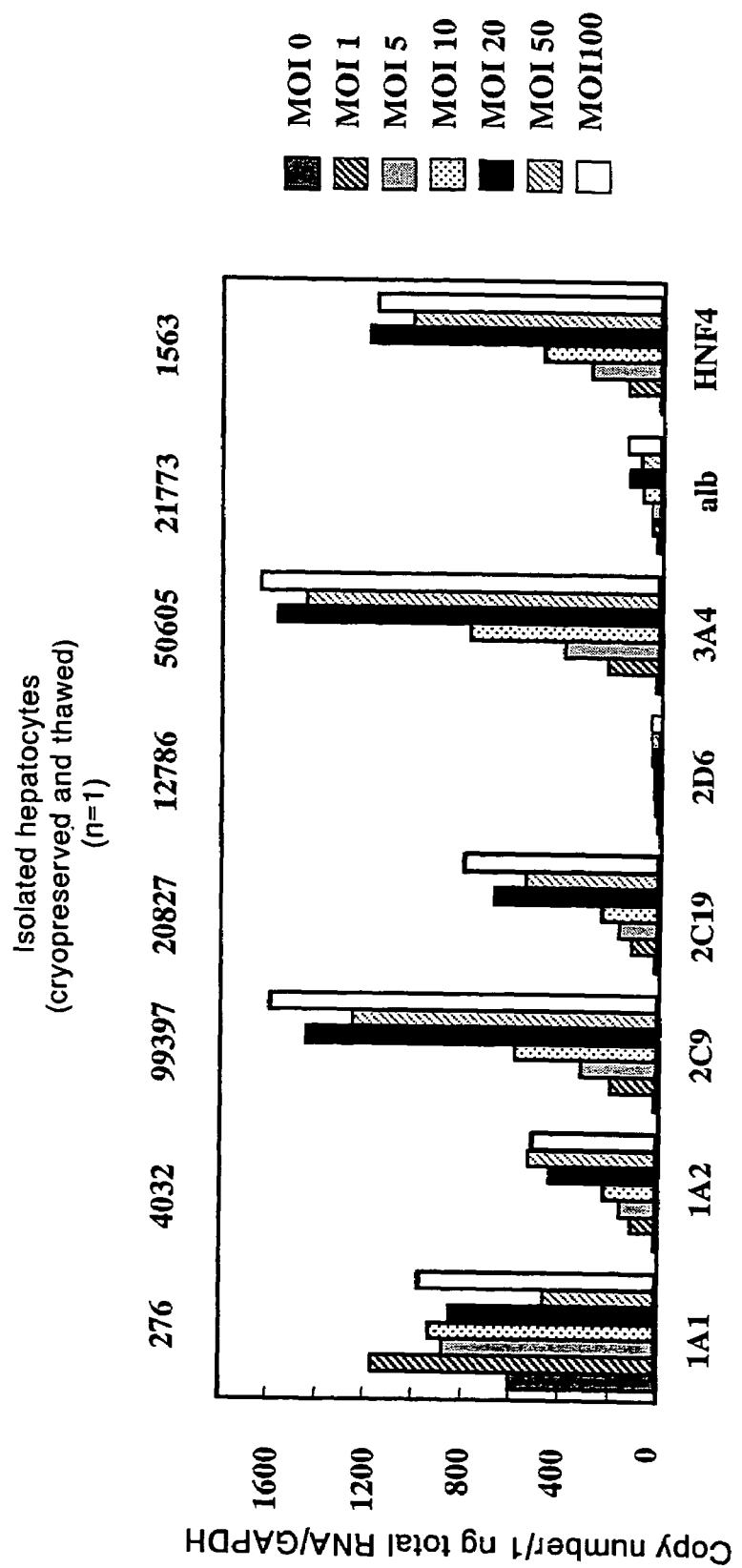
FIG. 10 is a graph showing expression of human P450 gene on cultured human cells, to which human HNF4 gene is introduced.

As the result, increase in the expression of human P450 gene was recognized with infective dose dependent manner (FIG. 10).

INDUSTRIAL APPLICABILITY

As explained in detail hereinabove, the present invention provides a monoclonal antibody which specifically recognizes proliferative human hepatocytes, proliferative human hepatocytes isolated by use of the antibody, and functional human hepatocytes obtained by differentiation induction of the cells.

The invention claimed is:

1. An antibody specifically recognizing proliferative human hepatocytes that exist in a hepatocyte population isolated from an adult human liver and have clonal proliferative ability and differentiation ability to functional hepatocytes, which antibody is produced by Mouse-Mouse hybridoma K8223 (FERM BP-8334).

2. A hybridoma cell producing the antibody of claim 1, which is Mouse-Mouse hybridoma K8223 (FERM BP-8334).

3. A method for isolating proliferative human hepatocytes, which comprises separating cells recognized by the antibody of claim 1, from a human hepatocyte population.

* * * * *